(12) United States Patent
Manion (10) Patent No.: US 9,476,835 B2
(45) Date of Patent: Oct. 25, 2016

(54) BIOLUMINESCENT PACKAGING

(75) Inventor: Michael Keoni Manion, Cronulla (AU)

(73) Assignee: Empire Technology Development LLC, Wilmington, DE (US)

( * ) Notice: Subject to any disclaimer, the term of this patent is extended or adjusted under 35 U.S.C. 154(b) by 743 days.

(21) Appl. No.: 13/519,877

(22) PCT Filed: Apr. 13, 2012

(86) PCT No.: PCT/US2012/033679
§ 371 (c)(1),
(2), (4) Date: Jun. 28, 2012

(87) PCT Pub. No.: WO2013/154590
PCT Pub. Date: Oct. 17, 2013

(65) Prior Publication Data
US 2013/0273554 A1    Oct. 17, 2013

(51) Int. Cl.
| | | |
|---|---|---|
| G01N 21/76 | (2006.01) |
| G01N 21/77 | (2006.01) |
| G01N 21/80 | (2006.01) |
| G01N 21/81 | (2006.01) |
| G01N 21/94 | (2006.01) |

(52) U.S. Cl.
CPC ............ *G01N 21/763* (2013.01); *G01N 21/77* (2013.01); *G01N 21/80* (2013.01); *G01N 21/81* (2013.01); *G01N 21/94* (2013.01); *G01N 2021/775* (2013.01)

(58) Field of Classification Search
None
See application file for complete search history.

(56) References Cited

U.S. PATENT DOCUMENTS

| | | | |
|---|---|---|---|
| 5,876,995 A | 3/1999 | Bryan |
| 6,544,729 B2 | 4/2003 | Sayler et al. |
| 2011/0217758 A1 | 9/2011 | Mertens et al. |

FOREIGN PATENT DOCUMENTS

| | | |
|---|---|---|
| CN | 102133977 | 5/2012 |
| MY | 145592 | 2/2012 |
| WO | WO 2010/092539 | 8/2010 |
| WO | WO 2011/045572 | 4/2011 |

OTHER PUBLICATIONS

Brovko, "Bioluminescence for Food and Environmental Microbiological Safety," //books.google.com.au/books?hl=en&lr=&id=5ddOoPqM6bwC&oi=fnd&pg=PR9&dq=Bioluminescence+for+Food+and+Environmental+Microbiological+Safety&ots=gcpUlgNGES&sig=KZ1iZOIxKFYgOJL7wf9GsB4HnM4&redir_esc=y#v=onepage&q=Bioluminescence%20for%20Food%20and%20Environmental%20Microbiological%20Safety&f=false.

"Ciba OnVu Smart Packaging Has Time-TemperatureIndicators," information was available at website: //www.matbase.com/Ciba_OnVu_smart_packaging_has_time-temperature_indicators, in some form no later than Jan. 16, 2012. While the website as it existed on Jan. 16, 2012, is not in Applicant's possession, Applicant has provided the website that was printed on Aug. 3, 2012.
Harman, "Australia: New Intelligent Food Packaging Will Warn Consumers of Product Freshness," information was available at website: http://www.just-food.com/news/new-intelligent-food-packaging-will-warn-consumers-of-product-freshness_id88574.aspx, in some form no later than Jan. 16, 2012. While the website as it existed on Jan. 16, 2012, is not in Applicant's possession, Applicant has provided the website that was printed on Aug. 3, 2012.
Mills, "Oxygen Indicator and Intelligent Inks for Packaging Food," Chem. Soc. Rev., 2005, pp. 1003-1011, vol. 34.
Miltz et al., "A Bioluminescence Method for the Determination of Oxygen Transmission Rates Through Plastic Films," J. Fd. Technology, 1980, pp. 389-396, vol. 15 (4).
Neethirajan et al., "Nanotechnology for the Food and Bioprocessing Industries," Food Bioprocess Technology, 2011, pp. 39-47, vol. 4 (1).
"Packaging Solutions with Human Intelligence!" information was available at website: //www.omegapackaging.com.au/packaging-related-useful-information/packaging-solutions-with-human-intelligence.html, in some form no later than Jan. 16, 2012. While the website as it existed on Jan. 16, 2012, is not in Applicant's possession, Applicant has provided the website that was printed on Aug. 3, 2012.
Siró, Active and Intelligent Packaging of Food, John Wiley & Sons, Ltd. (Published online Jan. 16, 2012), 26 pages.
"Smart Packaging Promises CSR Benefits," information was available at website: ://www.justmeans.com/Smart-packaging-promises-CSR-benefits/42282.html, in some form no later than Jan. 16, 2012. While the website as it existed on Jan. 16, 2012, is not in Applicant's possession, Applicant has provided the website that was printed on Aug. 3, 2012.
Yam et al., "Intelligent Packaging: Concepts and Applications," Journal of Food Science, 2005 , vol. 70, Nr. 1, (Published on web Dec. 22, 2004).
Asad et al., "Bench-to-Bedside Review: Quorum Sensing and the Role of Cell-to-Cell Communication During Invasive Bacterial Infection," Critical Care, 2008, pp. 1-11, vol. 12(236).
Biosensor Technology for Food Packaging Applications, Jan. 11, 2012, pp. 1-22.
Bai et al. "Bacterial Quorum Sensing and Food Industry," Comprehensive Reviews in Food Science and Food Safety, May 2011, pp. 183-193, vol. 10(3).
International Search Report and Written Opinion received in International Application No. PCT/US2012/033679, mailed on May 28, 2012, filed on Apr. 13, 2012.
Lin et al., Bacterial Bioluminescence—Biochemistry and Molecular Biology, Progen Biotech Inc., from the web site of Photobiological Sciences Online, Jan. 25, 2009, 32 pages. www.photobiology.info/Lin.html.
March et al., "Quorum Sensing and Bacterial Cross-Talk in Biotechnology," Current Opinion in Biotechnology, 2004, pp. 495-502, vol. 15.
Wu Shu-Hang et al., "Prospects of Applying Bioluminescence in Monitoring Agricultural Product Safety," Journal of Agro-Environment Science, 2006-S1, from the web site of China National Knowledge Infrastructure (CNKI), 2006, 4 pages. //en.cnki.com.cn/Article_en/CJFDTOTAL-NHBH2006S1096.htm.

*Primary Examiner* — Anand Desai
(74) *Attorney, Agent, or Firm* — Dorsey & Whitney LLP (57) ABSTRACT

Some embodiments provided herein relate to bioluminescent packaging, methods of making, and methods of sensing the state of a material. In some embodiments, light emitted by a bioluminescent organism can be used to sense the state of a material.

16 Claims, 3 Drawing Sheets

BIOLUMINESCENT PACKAGING

CROSS-REFERENCE TO RELATED APPLICATION

This application is the U.S. national phase entry under 35 U.S.C. §371 of PCT/US2012/033679, filed on Apr. 13, 2012, the entire disclosure of which is hereby incorporated by reference herein.

FIELD

Embodiments herein generally relate to bioluminescent packaging and uses thereof.

BACKGROUND

There area variety of packaging materials that can be used to store food and other materials in order to, for example, preserve and/or protect the material so stored. Generally, these materials attempt to preserve food by isolating the material from external sources of contamination, such as microorganisms.

SUMMARY

In some embodiments, a bioluminescent packaging is provided. The packaging can include a matrix and a population of one or more bioluminescent organism. In some embodiments, the population of bioluminescent organisms is configured to emit light that corresponds to a state of a material. In some embodiments, the population includes a quantity of bioluminescent organisms that is large enough to emit an observable light signal.

In some embodiments, a method of sensing a state of a material is provided. The method can include providing a material and a packaging that includes at least one bioluminescent organism. In some embodiments, the bioluminescent organism conditionally emits light based upon the state of the environment near the bioluminescent organism. The method can include placing the material near the environment of the bioluminescent organism and detecting the presence or absence of light emitted by the bioluminescent organism, thereby sensing a state of the material.

In some embodiments, a method of manufacturing a bioluminescent packaging is provided. The method can include providing at least one bioluminescent organism, providing a matrix, and combining the bioluminescent organism with the matrix, thereby producing a bioluminescent packaging.

The foregoing summary is illustrative only and is not tended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant, to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In some embodiments, bioluminescent packaging compositions, methods of sensing a state of a material, and/or methods of manufacturing a bioluminescent packaging are provided herein.

In some embodiments, the bioluminescent packaging includes at least one bioluminescent organism that contacts (for example, is supported by) a matrix. The bioluminescent packaging can include a permeable membrane that contacts the matrix, for example a membrane between the matrix and a packaged material (or a volume configured to hold the material). In some embodiments, the bioluminescent organism conditionally emits light in response to a state of the packaged material. For example, the state of the packaged material can include ripeness, spoilage, unreadiness, contamination, and/or if the package has been opened or a seal broken. Indicators of these states (for example, various gases or chemicals) can pass through the membrane and interact with the bioluminescent organism. In some embodiments, the organism senses the presence or absence of the indicators and will change their bioluminescent properties. In some embodiments, light emitted by the organism is detected, and is an indicator of a state of the material to be packaged.

Bioluminescent Packaging

In some embodiments, the bioluminescent packaging can include a matrix and a population of one or more bioluminescent organisms. In some embodiments, the population of organisms is configured to emit light which corresponds to a state of a material and the population includes a quantity of organisms sufficient to emit an observable light signal. In some embodiments, the amount of light emitted is sufficient to be observed by the unaided eye in normal, daylight conditions.

Figure 1:
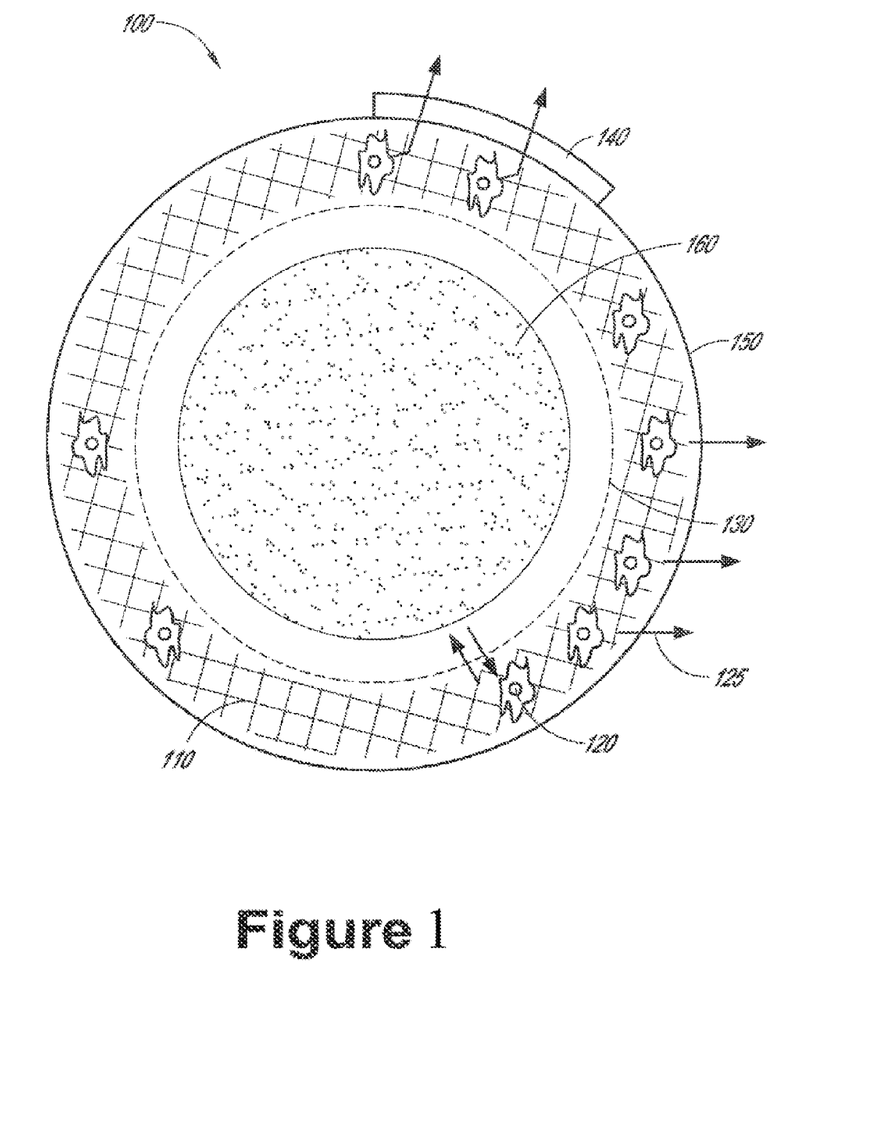
FIG. 1 is a drawing of some embodiments of a bioluminescent packaging.

FIG. 1 illustrates some embodiments of a bioluminescent packaging 100. The depicted packaging includes a matrix 110 and at least one bioluminescent organism 120. In some embodiments, the organism is configured to emit light 125, which corresponds to a state of a material. In some embodiments, the packaging includes a membrane 130. In some embodiments, the membrane 130 is gas-permeable and/or selectively permeable to other indicators from the material. In some embodiments, the membrane 130 contacts a surface of the matrix 110. In some embodiments, the membrane 130 contacts an inner surface of the matrix 110. In some embodiments, the bioluminescent packaging includes an optical filter 140 that is configured to change the color of light emitted by the bioluminescent organisms. In some embodiments, the bioluminescent packaging includes an optional outer membrane 150. In some embodiments, the bioluminescent packaging contains a packaged material 160.

In some embodiments, the bioluminescent packaging includes and/or is in the form of a film, a wrap, a spray, a spray-coat, a bag, a pouch, a container, a box, a tray, a canister, a bottle, a jar, or other packaging system or device.

In some embodiments, the packaging includes two or more of the listed structures, for example a tray covered by or a tray covered by a spray-coat.

In some embodiments, the bioluminescent packaging is configured to contain the material to be packaged in a substantially air-tight and/or liquid tight enclosure. In some embodiments, the bioluminescent packaging is configured to contain, but not form a seal around the material to be packaged, for example an open-topped canister, tray, or carton.

In some embodiments, the bioluminescent packaging includes or is a patch or sensor that is applied directly to the material to be packaged.

In some embodiments, the bioluminescent packaging includes an optical filter for changing the color of light emitted by the organism. Any optical filter can be employed. In some embodiments, the filter absorbs light at the wavelength emitted by the organism and emits light at a shifted wavelength. In some embodiments, the shift in wavelength allows for a more noticeable optical indicator of the luminescence of the organism.

In some embodiments, the bioluminescent packaging includes a biodegradable material and/or is compostable. In some embodiments, substantially all of the bioluminescent packaging is biodegradable.

In some embodiments, the bioluminescent packaging includes a matrix. In some embodiments, the matrix includes one or more of a starch, a carbohydrate, a nucleic acid, a polynucleotide, a peptide, a polypeptide, a protein, a synthetic polymer, a hydrogel, or a foam.

In some embodiments, the matrix includes at least one nutrient for the bioluminescent organism. In some embodiments, the matrix includes a food source for the bioluminescent organism. In some embodiments, the matrix includes at least one of a peptide, a casein peptone, a vitamin, a trace element, or a mineral.

In some embodiments, the matrix has a substantially uniform thickness. In some embodiments, the matrix is thicker in at least one area than in other areas (and thus need not be substantially uniform). In some embodiments, the average thickness of the matrix is at least about 0.05 millimeters, for example about 0.05 millimeters, 0.1, 0.15, 0.2, 0.25, 0.3, 0.4, 0.5, 1, 1.5, 2, 2.5, 3, 4, 5, 8, 9, 10, 1, 12, 13, 15, 17, 20, 25, 30, 35, 40, 50, 100, 150, or 200 millimeters, including ranges between any two of the listed values and any range above any one of these values.

In some embodiments, the matrix is at least partially transparent to electromagnetic radiation. In some embodiments, the matrix is at least partially transparent to visible light. In some embodiments, the matrix is at least about 1% transparent to light emitted by the bioluminescent organisms, for example at least about 1%, 5%, 10%, 20%, 30%, 40%, 50%, 60%, 70%, 80%, 90%, 95%, 97%, 98%, 99% or 100% transparent to light emitted by the bioluminescent organisms, including ranges between any two of the listed values.

In some embodiments, the matrix and/or bioluminescent organism is spread throughout the entire package. In some embodiments, the matrix and/or bioluminescent organism are only distributed in a subsection of the package (for example, just a lid or a section of a wall). In some embodiments, the matrix and/or bioluminescent organism is in less than 100% of the surface area of the packaging, for example, less than 99, 95, 90, 80, 70, 60, 50, 40, 30, 20, 10, 5, or 1% of the surface area is associated with the matrix and/or bioluminescent organism.

In some embodiments, the bioluminescent packaging includes at least one bioluminescent organism. In some embodiments, the bioluminescent organism contacts the matrix. In some embodiments, the bioluminescent organism is substantially embedded in the matrix.

In some embodiments, the bioluminescent organism includes at least one of the following organisms: Vibrionaceae, for example *Vibrio fisheri*, *Vibrio harveyi*, or *Vibrio phosphoreum*; Dinoflagellates, for example *Noctiluca scintillans*, or *Pyrodimium bahamense*; Schewanellaceae, for example *Shewanella hanedai*, or *Shewanella woodyi*; fungi, for example *Amillaria, Omphalotus, Mycena, Gerronema, Pleurotus*; marine vertebrate cells, for example fish cells; marine invertebrate cells; other vertebrate cells, for example frog cells; or other invertebrate cells, for example insect cells. In some embodiments, the bioluminescent organism includes a mixture of two or more organisms. In some embodiments, the organism is generally recognized as safe (GRAS) in at least one jurisdiction. In some embodiments, the organism is generally recognized as safe (GRAS) in all jurisdictions. In some embodiments, the organism is generally recognized as safe (GRAS) in the applicable jurisdiction.

In some embodiments, the bioluminescent organism is genetically modified or is a chimeric. In some embodiments, the bioluminescent organism includes a gene encoding luciferase. In some embodiments, the bioluminescent organism includes a gene encoding luciferin. In some embodiments, the bioluminescent organism includes the bacterial lux operon. In some embodiments, the bioluminescent organism includes a gene encoding an inducer of luciferase, and/or luciferin. In some embodiments, the inducer is a transcription factor. In some embodiments, the inducer is expressed (or is effectively expressed) in the presence of an environmental condition. In other embodiments, the inducer is primarily (or only) expressed in the absence of an environmental condition. In some embodiments, the inducer is primarily (or only) functional in the presence of an environmental condition. In other embodiments, the inducer is primarily (or only) functional in the absence of an environmental condition.

In some embodiments, the bioluminescent organism emits light of at least one wavelength. In some embodiments, the emitted light is in the visible spectrum. In some embodiments, the light at least has a wavelength of about 380 nanometers to about 800 nanometers, for example, about 380 nanometers, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 nanometers, including ranges between any two of the listed values. In some embodiments, different colors can be used for various indication purposes. Thus, in some embodiments, a collection of organisms can be included, each set up to detect a specific aspect and provide a corresponding specific bioluminescence signal, such as a red light or green light. In some embodiments, a single type of organism can be configured to detect various aspects and respond with specific bioluminescence signals. In some embodiments, this can be done through engineering the organism to produce light at these wavelengths, and/or by including a filter. In some embodiments, the organism emits light of two or more wavelengths, e.g., the entire general spectrum.

In some embodiments, a population of bioluminescent organisms is provided. In some embodiments, the size of the population is sufficient to emit an observable light signal without the aid of a device. In some embodiments, the population includes at least about $10^3$ organisms, for example about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, or $10^{17}$ organisms, including ranges between any two of the listed values. In some embodiments, lower amounts can be used, and need not be visible to the unaided human eye.

In some embodiments, the density of the bioluminescent organisms in the matrix exceeds the minimum density needed for quorum sensing. The minimum density needed for quorum sensing depends upon the type of organism. For example, for Vibrio fisheri under laboratory conditions, the minimum density required for quorum sensing is about $10^{11}$ cells per milliliter (cells/ml). In some embodiments, the density of the bioluminescent organism is at least about $10^7$ cells/ml, for example about $10^7$, $10^8$, $10^9$, $10^{10}$, $10^{11}$, $10^{12}$, $10^{13}$, $10^{14}$, or $10^{15}$ cells/ml, including ranges between any two of the listed values. In some embodiments, the organisms are of substantially the same density throughout the matrix. In some embodiments, some portions of the matrix contain the organism at higher density than other portions. For example, a patch or a section of the matrix located beneath a viewing window and/or filter includes organisms at a density that exceeds the minimum density for quorum sensing, while the rest of the matrix includes organisms at a lower density, or includes substantially no organisms. In some embodiments, a local density can be greatly higher than the average density, so as to allow even easier observation of the conditions of the material. Such areas can also be indicated on the package, so that a user's attention is directed to the specific areas that could be very bright depending upon the state of the material.

In some embodiments, the bioluminescent organism is in a metabolically quiescent state. In some embodiments, the metabolically quiescent state is a "live but not replicating (LNR)" state. In some embodiments, the LNR state provides reduced replication by the microorganism. In some embodiments, the LNR state includes a replication rate that is no faster than about $5 \times 10^{-1}$, $1 \times 10^{-1}$, $1 \times 10^{-2}$, $1 \times 10^{-3}$, $1 \times 10^{-4}$, $1 \times 10^{-5}$ or $1 \times 10^{-6}$ of the replication rate of the microorganism cultivated on rich medium in a normal, non-metabolically quiescent state. In some embodiments, the state is such that there is effectively no replication of the organisms. In some embodiments, the metabolically quiescent state includes a state of nutrient deprivation. In some embodiments, the metabolically quiescent state is metabolic hibernation. In some embodiments, the metabolically quiescent state is reversible so that the organism will exit the metabolically quiescent state and return to metabolically active state. In some embodiments, the microorganism is initially in a metabolically quiescent state, but can become activated as the environment near the packaged material changes. In some embodiments, a substance secreted by the packaged item induces the microorganism to exit the metabolically quiescent state. In some embodiments, oxygen induces the organism to exit the metabolically quiescent state. In some embodiments, carbon dioxide induces the organism to exit the metabolically quiescent state. In some embodiments, the organism is genetically modified to enter a quiescent state. In some embodiments, the presence of a particular indicator from the packaged material can shift the organism from the quiescent state.

In some embodiments, the bioluminescent organism produces a reporter. In some embodiments, the presence of the reporter indicates a state of the material or environment. In some embodiments, the absence of the reporter indicates a state of the material or the environment. In some embodiments, the reporter is a gene product. In some embodiments, the reporter includes a product of the bacterial lux operon. In some embodiments, the reporter includes a luminescent molecule, for example luciferase. In some embodiments, the reporter is an endogenous gene product, for example Vibrio fisheri expressing endogenous luciferase. In some embodiments, the reporter is produced by a transgene, for example an insect cell line expressing renilla luciferase or firefly luciferase.

In some embodiments, organism expresses a fluorescent molecule, for example a fluorescent protein such as green fluorescent protein (GFP), yellow fluorescent protein (YFP), red fluorescent protein (RFP), or cyan fluorescent protein (CFP). The fluorescent molecule absorbs light of first a wavelength produced by the organism, and emits light of a second wavelength. In some embodiments, the bioluminescent organism expresses two or more fluorescent molecules. In some embodiments, the bioluminescent organism expresses a first fluorescent molecule that is a FRET donor, and a second fluorescent molecule that is a FRET acceptor. In some embodiments, the bioluminescent organism primarily expresses a fluorescent molecule or combination of fluorescent molecules under certain environmental conditions. In some embodiments, the fluorescent molecule is produced in addition to a luminescent gene product such as luciferase. In some embodiments, the organism produces a luminescent molecule, and the reporter includes a fluorescent molecule. In some embodiments, the organism produces one or more fluorescent molecules as reporters of additional state or sub-states of the material being packaged. For example, the organism can continuously produce firefly and renilla luciferase, thus emitting blue light. When the state of a material is sensed as desirable (for example, ripe), the organism expresses GFP, and thus emits green light. When the state of the material to be sensed is undesirable (for example, spoiled), the organism expresses RFP, and thus emits red light.

In some embodiments, the bioluminescent organism emits light corresponding to a state of a material. In some embodiments, the presence of light corresponds to the state of the material. In some embodiments, the absence of light corresponds to the state of the material. In some embodiments, the light emitted by an organism depends upon the environment proximate to the organism, and the material is within that environment. In some embodiments, the environment proximate to the organism includes space within at least about 1 millimeter of the organism, for example about 1 millimeter, 2, 3, 5, 10, 20, 30, 40, 50, 60, 70, 80, 90, 100, 120, 150, 200, 300, 400, or 500 millimeters of the organism.

In some embodiments, the condition of the environment proximate to the material and therefore the environment proximate to the organism, when the material is in the environment proximate to the organism) depends on the state of the material. In some embodiments, the material is in the environment proximate to the microorganism, and the state of the material is thus sensed by the microorganism. In some embodiments, the state of the material is a state that is desirable to a user of the material. In some embodiments, the state of the material is a state that is undesirable to a user of the material. In some embodiments, the state of the material is one of ripening, maturing, ready-to-use, expired, contaminated or infected (for example, by a parasite such as mold or bacteria, or by a toxin). In some embodiments, the state of the material is a temperature, humidity, pH, oxygen content, and/or $CO_2$ content that is either within or outside of a desired range. In some embodiments, the state of the material is two or more of the listed states, provided such states are not mutually exclusive.

In some embodiments, light emitted by the organism depends on the presence of a molecule or combination of molecules (for example, an indicator molecule) in the environment proximate to the organism. In some embodiments, light emission is induced by the presence of the molecule, while in some embodiments, light emission is inhibited by the presence of the molecule.

In some embodiments, the molecule includes at least one of water, oxygen, carbon dioxide, a proton, ethanol, ethylene, a sugar (for example glucose, galactose, fructose, sucrose, or mannose), a decay factor, an inorganic molecule, a hormone, or a contaminant. For example, a ripe fruit may produce ethylene, which then contacts the organism and causes the organism to glow. In some embodiments, a sealed package can be breached, introducing oxygen and causing the organism to glow. In some embodiments, there is a threshold concentration of the molecule. In some embodiments, light is only produced when the concentration is below the threshold, while in some embodiments, light is only produced when the concentration is above the threshold. In some embodiments, the threshold concentration is at least about 0.1 micromolar ($\mu$M), for example about 0.1 $\mu$M, 0.2, 0.3, 0.5, 1, 1.5, 2, 3, 4, 5, 10, 20, 30, 40, 50 70, 100, 150, 200, 300, 400, 500, 600, 700, 800, 900, 1,000, 2,000, 3,000, 4,000, 5,000, 7,000, 10,000, 20,000, 50,000, 100,000, 200,000, 300,000, 500,000, 700,000, or 1,000,000 $\mu$M, including ranges between any two of the listed values.

In some embodiments, the light emitted by the organism is induced by a specific temperature or temperature range in the environment proximate to the organism. In some embodiments, light is emitted when the environment is above a threshold temperature. In some embodiments, light is emitted when the environment is below a threshold temperature. In some embodiments, the threshold temperature is at least about $-10°$ C., for example about $-10°$ C., $-5$, 0, 5, 10, 15, 20, 21, 22, 23, 24, 25, 26, 27, 28, 29, 30, 31, 32, 33, 34, 35, 36, 37, 38, 39, 40, 42, 45, 50, 55, 60, 65, 70, 75, or 80° C., including ranges between any two of the listed values and any range above any one of the values.

In some embodiments, the light emitted by the organism is induced by a specific humidity or humidity range in the environment proximate to the organism. In some embodiments, light is emitted when the environment is above a threshold humidity. In some embodiments, light is emitted when the environment is below a threshold humidity. In some embodiments the threshold relative humidity the ratio of partial pressure of water vapor in the environment to the saturated pressure of water vapor at the same temperature) is at least about 5%, for example about 5%, 10%, 15%, 20%, 25%, 30%, 40%, 50%, 60%, 70%, 80%, 85%, 90%, 95%, or 99%, including ranges between any two of the listed values.

In some embodiments, the light emitted by the organism is induced by a specific pH in the environment proximate to the organism. In some embodiments, the pH is no more than about 2, for example about 2, 2.5 3, 3.5, 4, 4.5, 5, 5.5, 6, 6.5, or 7, including ranges between any two of the listed values. In some embodiments, the pH is at least about 7, for example about 7, 7.5, 8, 8.5, 9, 9.5, 10, 10.5, 11, 11.5, or 12 including ranges between any two of the listed values.

In some embodiments light is emitted in response to a combination of two or more of the listed environmental conditions, for example a combination of temperature and humidity.

In some embodiments, the health of the organism follows the integrity of the material within the packaging. Thus, in some embodiments, the organisms in the packaging start off healthy and strong and with a large amount of bioluminescence. In some embodiments, as the material in the package begins to decompose, decomposed material (or waste products from any contaminating bacteria on the material) can contact the organisms and results in their death, thereby reducing the bioluminescence. Thus, a bioluminescent package with no or low bioluminescence is indicative of a decomposing material within the packaging. In some embodiments, the population and/or density of the organism is what indicates the status of the material inside. For example, the decomposing material can provide nutrients to the organisms and/or rescue the organisms from a quiescent state, causing them to increase in number and resulting in greater luminescence. Thus, in some embodiments, an increase in luminescence can indicate decomposition of the material.

In some embodiments, when the cells are in the LNR state, they are quiescent. The change in the condition (for example, increased oxygen, temperature, moisture, ethylene, etc) causes the cells to become metabolically active, and thus produce light. In some embodiments, one can culture the cells to become active at a particular threshold for the condition desired, before inducing them into the LNR state. This can involve, for example with ethylene, growing them in a concentration of ethylene and restricting other carbon sources such that this becomes their preferred carbon source. In some embodiments, one can induce them to become obligate metabolisers of that carbon source. This can be done (or such cells can be selected for) the other conditions, and can be used to make them either switch on at a certain threshold, or switch off at the threshold, depending on the application, in some embodiments, the bioluminescence aspects of the microorganisms can be accomplished with genetic engineering. In some embodiments, one can use the matrix to respond to the condition (for example, pH, temperature, etc), to liberate a compound (such as a food and/or carbon source) which can then induce (or inhibit) the organisms to produce light.

In some embodiments, the bioluminescent packaging includes a membrane. In some embodiments, the membrane is substantially permeable to a gas and/or a liquid. In some embodiments, the membrane contains pores that permit the passage of gas and/or liquid, and/or various molecules. The pores can be substantially the same size, or of a variety of sizes. The pores can have an average diameter of at least about 0.01 micrometers, for example about 0.01, 0.05, 0.1, 0.15, 0.2, 0.25, 0.3, 0.4, 0.5, 1, 1.5, 2, 2.5, 3, 4, 5, 6, 7, 8, 9, 10, 11, 12, 13, 15, 17, 20, 25, 30, 35, 40, 50, 100, 150, 200, 500, or 1000 micrometers, including any range between any two of the listed values and any range above any one of these values. In some embodiments, the membrane has a substantially uniform thickness. In some embodiments, some portions of the membrane are thicker than others. In some embodiments, the average thickness of the membrane is at least about 0.01 millimeter, for example about 0.01, 0.05, 0.1, 0.15, 0.2, 0.25, 0.3, 0.4, 0.5, 1, 1.5, 2, 2.5, 3, 4, 5, 6, 7, 8, 9, 10, 11, 12, 13, 15, 17, 20, 25, 30, 35, 40, or 50 millimeters, including ranges between any two of the listed values.

In some embodiments, the membrane substantially covers a surface of the matrix. In some embodiments, the membrane covers at least about 1% of the surface of the matrix, for example at least about 5%, 10%, 20%, 30%, 40%, 50%, 60%, 70%, 80%, 90%, 95%, 98%, 99%, or 99.9%. In some embodiments, the membrane covers the surface of the matrix proximal to the material being packaged, for example an inner surface. In some embodiments the membrane can be reflective to deliver more light to the outer surface, and thus increase the signal. FIG. 1 illustrates a membrane 130 that is proximal to the material being packaged. In other embodiments, the membrane covers the surface of the matrix distal to the item material being packaged, for example an outer surface. In some embodiments, an outer surface of the matrix is sealed, such that gas and other molecules do not inadvertently come into contact with the organisms (apart from those from within the container). In some embodiments, the membrane substantially coats a surface of the matrix distal to the material being packaged. FIG. 1 illustrates an outer membrane 150 that is distal to the material being packaged. In some embodiments, the packaging material optionally includes two or more membranes. In some embodiments, the material includes a first inner membrane 130 that is proximal to the material being packaged, and a second outer membrane 150 that is distal to the material being packaged. In some embodiments, a membrane positioned distally to the packaged material is optionally permeable to gas. In other embodiments, a membrane positioned distally to the packaged material is substantially impermeable to gas.

In some embodiments, a membrane positioned proximally to the packaged material, or a portion of this membrane is optionally at least partially transparent to light emitted by the bioluminescent organism. In some embodiments, a membrane positioned proximally to the packaged material is substantially opaque to light emitted by the bioluminescent organism. In some embodiments, a membrane positioned distally to the packaged material includes at least a portion that is at least partially transparent to light emitted by the bioluminescent organism. In some embodiments, the partially transparent portion of the membrane is at least about 1% transparent to light emitted by the bioluminescent organism, for example at least about 1%, 5%, 10%, 20%, 30%, 40%, 50%, 60%, 70%, 80%, 90%, 95%, 97%, 98%, 99%, or 100% transparent to light emitted by the bioluminescent organisms, including any range between any two of the listed values. In some embodiments, only a portion of the membrane is transparent to light emitted by the bioluminescent organism, for example, a viewing window. In some embodiments, two or more portions of the membrane are transparent to light emitted. In some embodiments, the transparent portion of membrane includes at least about 1% of the surface area of the membrane, for example, about 1%, 2%, 3%, 5%, 10%, 20%, 30%, 40%, 50%, 60%, 70%, 80%, 90%, 95%, 97%, 98%, 99%, or 100%.

In some embodiments, the packaging includes a light filter. In some embodiments, the filter contacts a surface of the matrix. In some embodiments, the filter is embedded in the matrix. In some embodiments, the filter is the surface of the matrix distal to the packaged material. In some embodiments, the filter contacts a membrane (inner or outer) that covers the matrix. In some embodiments, the filter covers at least a portion of the membrane, for example a viewing window. In some embodiments, the filter is embedded in the membrane, in some embodiments, the filter is positioned between the membrane and the bioluminescent organism, in some embodiments, the membrane is positioned between the filter and the bioluminescent organism. In some embodiments, the filter can be positioned between the organism and a viewer.

In some embodiments, the filter permits a single and/or select range of wavelengths of light to pass. In some embodiments, the filter permits two or more ranges of wavelengths of light to pass, and the two or more ranges do not overlap. In some embodiments, the filter permits the passage of wavelength range of no more than about ±30 nanometers, for example about ±30 nanometers, 27, 25, 22, 20, 18, 15, 12, 11, 10, 9, 8, 7, 6, 5, 4, 3, 2, 1, or 0.5 nanometers, included ranges between any two of the listed values. In some embodiments, the midpoint of the range of wavelengths permitted to pass through the filter is about 480 nanometers. In some embodiments, the midpoint of the range of wavelengths permitted to pass through the filter is one of about 380 nanometers, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 nanometers. By using such filters, the apparent color that is observed can be clarified by the removal of other, neighboring wavelengths of light.

In some embodiments, the color of light permitted to pass through the filter corresponds to the type of state indicated. For example, when the bioluminescent organism is configured to produced light when the state of the material is desirable (e.g. fresh, or ready-to-use), the filter may permit only green light to pass (e.g. wavelengths of about 510 nm to about 550 nm).

In some embodiments, a method of sensing a state of a material is provided. In some embodiments, the method includes providing a material that is to be monitored. In some embodiments, the method includes providing a packaging that contains least one bioluminescent organism, as described herein. The bioluminescent organism conditionally emits light based upon a state of an environment proximal to the bioluminescent organism. In some embodiments, the method includes placing the material near the environment of the bioluminescent organism. In some embodiments, the method includes detecting the presence or absence of light emitted by the bioluminescent organism. In some embodiments, the method thus senses the state of the material.

Figure 2:
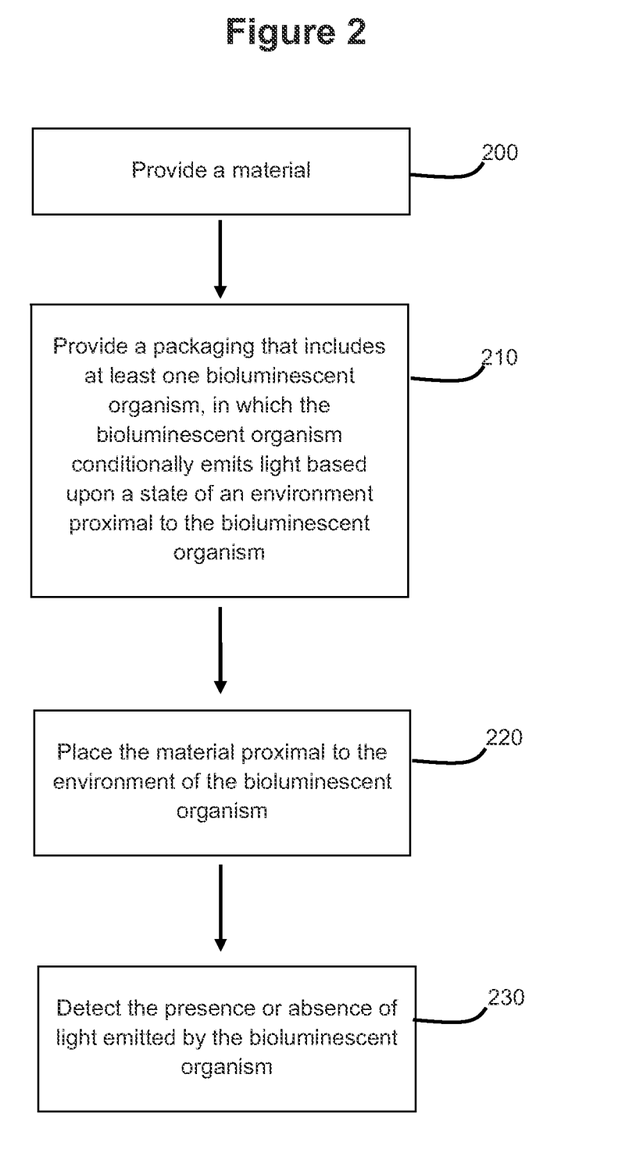
FIG. 2 is a flow diagram depicting some embodiments of sensing a state of a material.

FIG. 2 is a flow diagram illustrating a method of sensing a state of a material. A material can be provided 200. A packaging that includes at least one bioluminescent organism, in which the bioluminescent organism conditionally emits light based upon a state of an environment proximal to the bioluminescent organism, can be provided 210. The material is placed proximal to the environment of the bioluminescent organism 220. The presence or absence of light emitted by the bioluminescent organism is detected 230.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In some embodiments, the material is a material to be packaged. In some embodiments, the indicator indicates the state of the packaging, and thus allows for inferring of the state of the material In some embodiments, the material is at least one of a food, a beverage, a pharmaceutical composition, an agricultural product, a biological specimen, a transplantable organ, a transplantable tissue, or a forensic sample.

In some embodiments, the state of the material to be indicated is as described herein, for example at least one of maturing, ready-to-use, or expired. In some embodiments, the state of the material is as described herein, for example at least one of temperature, humidity, or temperature and humidity.

In some embodiments, the state of the material is a state of high temperature. In some embodiments, a state of high temperature is at least about 1° C., for example about 1° C., 2, 3, 5, 10, 15, 20, 10, 15, 20, 21, 22, 23, 24, 25, 26, 27, 28, 29, 30, 31, 32, 33, 34, 35, 36, 37, 38, 39, 40, 42, 45, 50, 55, 60, 65, 70, 75, or 80° C., including ranges between any two of the listed values.

In some embodiments, the state of the material is a state of low humidity. In some embodiments, a state of low humidity is a relative humidity of no more than about 50%, for example about 50%, 45%, 40%, 35%, 30%, 25%, 20%, 15%, 10%, 5%, or 1%.

In some embodiments, light emitted by the bioluminescent organism or the absence thereof is indicative of the state of the material as described herein. In some embodiments, the presence of light indicates the state of the material. In some embodiments, the absence of light indicates the state of the material. In some embodiments, the intensity of light indicates the state of the material. In some embodiments, the color of light indicates the state of the material.

In some embodiments, the material provides a source of nutrients for the bioluminescent organism, as described herein.

In some embodiments, the bioluminescent organism changes its luminescence is response to a change in the proximate environment as described herein. In some embodiments, the change in the proximate environment is a change in at least one of glucose levels, carbohydrate levels, oxygen, carbon dioxide, decay factors, or ethylene, in the packaged material, and the bioluminescent organism changes its luminescence in response to a change in at least one of the listed factors.

In some embodiments, the method of sensing a state of material includes providing a material and providing a packaging that includes at least one bioluminescent organism. In some embodiments, the bioluminescent organism conditionally emits light based upon a state of an environment proximal to the bioluminescent organism. The method can also include placing the material proximal to the environment of the bioluminescent organism. The method can also include detecting the presence or absence of light emitted by the bioluminescent organism. As described herein, the method thus senses a state of the material.

In some embodiments, a method of manufacturing a bioluminescent package is provided. In some embodiments, the method includes providing at least one bioluminescent organism, providing a matrix, and combining the bioluminescent organism with the matrix to provide the bioluminescent package.

Figure 3:
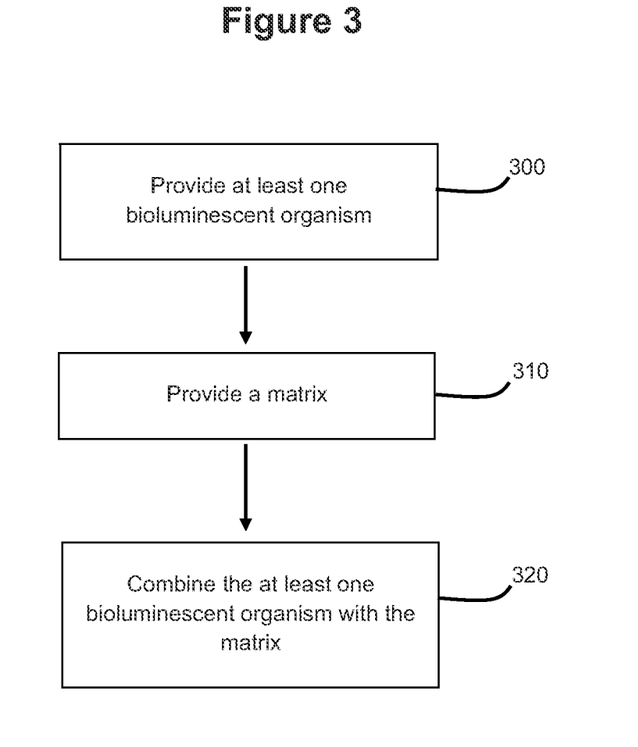
FIG. 3 is a flow chart depicting some embodiments of manufacturing a bioluminescent packaging.

FIG. 3 illustrates a method of manufacturing a bioluminescent package. In some embodiments, the method includes providing at least one bioluminescent organism 300. In some embodiments, the method includes providing a matrix 310. In some embodiments, the method includes combining the bioluminescent organism or organisms with the matrix 320.

In some embodiments, the bioluminescent organism is cultured in at least one batch. In some embodiments, two or more batches of bioluminescent organism are cultured and then combined. In some embodiments, after culturing, the bioluminescent organisms are purified. In some embodiments, the bioluminescent organisms are stored, for example by freezing. In some embodiments, the bioluminescent organisms are induced into a metabolically quiescent state. The metabolically quiescent state can be induced after a sufficient quantity of bioluminescent organisms has been cultured. In some embodiments, the metabolically quiescent state is a "live but not replicating state." In some embodiments, a metabolically quiescent state is induced by nutrient deprivation, oxygen deprivation, incubating the organism at a temperature outside of its normal growth range, genetic modification, or chemical modification, for example introducing a mutation or a small molecule that disrupts the normal progression of the cell cycle. In some embodiments, the bioluminescent organism provided includes *Vibrio fisheri*.

In some embodiments, the method includes providing a matrix. In some embodiments, the matrix is as described herein. In some embodiments, a matrix precursor is provided and a matrix is prepared from the precursor. In some embodiments, a solvent is added to the matrix precursor. In some embodiments, the matrix precursor is cross-linked.

In some embodiments, the matrix or matrix precursor is mixed with the organism and then applied to the packaging. In some embodiments, the matrix is applied to the packaging, and then the organism is added to the matrix. In some embodiments, the organism is spread onto a surface of the matrix. In some embodiments, the organism is embedded into the matrix, for example by injection, or by mixing.

In some embodiments, the bioluminescent organism is restrained to the matrix. For example, the bioluminescent organism can be embedded in the matrix, cross-linked to the matrix, covalently tethered to the matrix, and/or restrained on the matrix electromagnetically. In some embodiments, at least one bioluminescent organism that is not restrained to the matrix is washed away. For example, excess bioluminescent organisms can be washed away. In some embodiments, the organism is washed away with a solvent, for example water. In some embodiments, the water is pressurized. In some embodiments, the organism is washed away with a jet of gas. In some embodiments, the organism is washed away by aspiration. In some embodiments, the organism is washed away using electromagnetic force to collect the organism. In some embodiments, two or more of the above-listed methods are used to wash away the organism.

In some embodiments, a surface of the matrix is contacted with a membrane. In some embodiments, the membrane is as described herein. Inn some embodiments, the membrane is permeable to liquid and/or gas. In some embodiments, the membrane is an inner membrane to be positioned between the matrix and the material to be packaged ("proximal" to the material). In some embodiments, the membrane is an outer membrane to be positioned on a surface of the matrix distal to the material to be packaged. Such an outer membrane, or a portion thereof, can be at least partially transparent to light emitted by the bioluminescent organism. In some embodiments, the membrane is formed into a shape or mold, and the matrix is then applied to the membrane. In some embodiments, the matrix is contacted to the membrane, and the matrix and membrane are then shaped or molded, for example as a wrap or film to cover a packaged item. In some embodiments, the membrane is applied to the material to be packaged, for example as a protective, gas-permeable coat, and the matrix is then applied. In some embodiments, the matrix is applied to a membrane by spreading, pouring, injecting, or applying as a spray-coat. In some embodiments, after the matrix is applied, it is hardened or cured, for example by cross-linking.

In some embodiments, two or more surfaces of the matrix are each contacted by a membrane, for example an inner membrane to be positioned proximal to the packaged material, and an outer membrane to positioned distal to the material to be packaged. In some embodiments, two or more membranes are contacted to the matrix one surface at a time. In some embodiments, two or more membranes are contacted to the matrix simultaneously.

In some embodiments, a filter for changing the color of light emitted by the organism is contacted and/or attached to the matrix. In some embodiments, the filter is positioned on a surface of the matrix. In some embodiments, the filter is embedded in the matrix. In some embodiments, at least one membrane is positioned between the filter and the matrix. In some embodiments, the filter includes a molecule that is distributed throughout the matrix.

In some embodiments a bioluminescent packaging which holds a colony of *Vibrio fisheri* in a thin matrix in contact with food, such as being embedded within a semi-permeable barrier on the inside of a container is provided. In some embodiments, the light emitted serves to act as an attractive indicator to a consumer as to the state of the article in the packaging. This can be apparent when the container is opened, for example, if the package is opaque, or even before opening, for example if the package is transparent.

In some embodiments, the colony is actively metabolizing, although non-replicating, maintained through the provision of nutrients and co-factors embedded in the matrix and/or the food, and established at a concentration which is above that required for quorum sensing. In some embodiments, the filters can change the shape of the light being emitted.

In some embodiments, in addition to being bioluminescent, the microorganisms chosen for different applications are responsive to a relevant element. For example, the microorganisms may be responsive to something that is present in the food when it is fresh, and bioluminescent accordingly. This element may be a substance, such as glucose, or another carbohydrate which the organism preferentially metabolizes. Alternatively, the element may be a condition, such as the oxygen tension, or pH, of the environment within the package. Furthermore, the system can be devised such that the microorganisms glow in response to the food not being fresh. For example, they can respond to the presence of an element such as a decay factor, or something given off by the food, such as ethylene, when it becomes stale or over-ripe. Alternatively, the conditions inside the package may trigger the cells to begin to luminesce, due to the presence of oxygen (e.g. if the seal is broken), or a pH change.

In some embodiments, the matrix includes the microorganisms, together with an extracellular matrix, and some basic nutrients and salts, in order to maintain viability, such as: peptides and casein peptones; vitamins (including B vitamin); trace elements (e.g. nitrogen, sulphur & magnesium); and/or minerals.

As noted herein, the extracellular matrix can be made from a variety of materials, such as crosslinked starches or other carbohydrates, it is possible to make this with other materials, such as polynucleotides, or proteins, or other synthetic polymers. In some cases, this matrix can be a hydrogel. The matrix is most typically mixed with the microorganisms before polymerization/crosslinking, and then sprayed onto the inner barrier using spray coating techniques. In some cases, the matrix is crosslinked after application, such as by adding a crosslinking agent which specifically bonds the matrix polymers together, or specifically polymerizes the matrix material. In some cases, this is accomplished by heating and/or drying the matrix material, although the viability of the microorganisms can also be taken into account with these methods. An outer coating can then be applied. This is typically a thin film which is transparent, or semitransparent, applied as a spray coating, or wrapped film such as a shrink wrapping. In some cases, this film can be continually transparent, or may be opaque in regions to provide for light emission in certain areas of the packaging, whilst occluding others. The transparent regions may also have selective filters for producing a light effect of different colors in certain areas of the packaging. In some embodiments, this coating serves to separate the microorganisms from the food, and to provide for a semi-permeable barrier to allow for the exchange of the element within the food and/or the environment. In some cases, this may prevent the exchange of factors given off by the microorganisms from exchanging with the food.

An alternative approach is to adapt methodologies such as described in US2011/0217758, wherein the microorganisms are directly embedded within the polymer matrix. By including factors for survival and bioluminescence of the organism, and by providing for a transparent polymer matrix, permeable to at least the factor of interest for the food indicator, the container itself can be used as the matrix to support the microorganisms. The attractiveness of this approach is a lowered cost, and simplified processing.

In some embodiments, the packaging is provided as a food indicator, which is readily understood by the consumer, due to the glowing light. This can be used either as a positive indicator, to provide for an attractive light, demonstrating the freshness of the food, or a negative indicator, to provide a warning light (e.g. a red hue), which indicates that the food may not be safe to consume.

EXAMPLES

Example 1

Bioluminescent Packaging and Use Thereof

A melon is wrapped in a wrap that is a bioluminescent package. The wrap includes an inner membrane positioned proximal to the melon, a matrix, and an outer membrane. The inner membrane is 0.1 mm thick and made of paraffin wax. The inner membrane includes gas-permeable pores that pass through that membrane, cover 2% of the membrane surface, and have an average diameter of 0.5 mm.

The matrix is a gel that includes starch, glucose, and casein peptone. The matrix has a substantially uniform thickness and is about 5 mm thick, on average. The matrix is about 90% transparent to visible light. *Vibrio fisheri* are embedded throughout the matrix at a density of about $5 \times 10^{11}$ cells/ml. The entire packaging has about $10^{12}$ *Vibrio fisheri* total. The *Vibrio fisheri* are in a live but not replicating state.

The outer surface of the matrix (the surface distal to the melon) is covered in a membrane that has an average thickness of about 2 mm, and is about 95% transparent to visible light. A portion of the membrane that covers about 2 $cm^2$ of the membranes surface is covered by a filter that only permits the passage of light having a wavelength of about 460 to 500 nm.

As the melon ripens, it emits ethylene, which passes thought the inner membrane and contacts the *Vibrio fisheri*. Thus, ethylene is an indicator that the melon is in a ripe state. When the concentration of ethylene proximal to the *Vibrio fisheri* increases, the *Vibrio fisheri* increase their expression of products of the lux operon. The *Vibrio fisheri* thus emit light having a wavelength of about 480 nm. Thus, when the light is observed, the ripe state of the melon is indicated.

Example 2

Sensing the State of a Material

A 1 kg brick of cheese is provided. A packaging in the form of a pouch is provided. The packaging contains yeast (*Saccharomyces cerevisiae*) cells that express inducible products of the bacterial lux operon. The luciferase is configured to only be expressed in the presence of a peptide secreted by *Escherichia coli* (*E. coli*). The yeast cells are embedded in a matrix, which has an average thickness of about 1 mm, and an average yeast cell density of $10^9$ cells/ml. The matrix includes yeast extract, glucose, and bacto peptone. The inner (proximal) surface of the matrix is covered by a synthetic polymer film that is liquid-permeable, and is about 90% transparent to visible light. The outer surface of the matrix is covered by a synthetic polymer film that is substantially impermeable to gas and liquid, and is about 90% transparent to visible light.

When the pouch is sealed, it is substantially air-tight, but it permits the exchange of gas between the cheese and the matrix. The cheese is sealed in the pouch, so that the matrix is within 5 mm of the cheese.

After two weeks, the cheese becomes contaminated with *E. coli*, which secretes a unique peptide. The peptide passes through the inner membrane to the matrix. When the concentration of *E. coli* peptide increases, expression of products of the lux operon is increased in the yeast cells, so that greater amounts of luciferase, luciferin, and substrate are produced. The yeast cells thus emit blue-green light. The light passes through the outer membrane and is observed by a consumer. The consumer sees the light, and recognizes it as a signal that the cheese is contaminated by *E. coli*. The consumer disposes of the cheese.

Example 3

Method of Manufacturing a Bioluminescent Material

A 2 L batch of *V. fisheri* is cultured to a density of $10^{10}$ cell/ml. The *V. fisheri* are washed, and induced into a live but not replicating state. The *V. fisheri* are resuspended in a matrix precursor at a density of $10^{12}$ cells/ml. The matrix precursor is a liquid that contains starch, peptides, and glucose. A double-walled plastic canister with a volume of about 1 L is prepared, with a 2 mm space between the walls. The inner wall of the canister is gas-permeable and has an average thickness of about 3 mm. The outer wall of the canister is substantially importable to gas, has an average thickness of about 3 mm, and is 98% transparent to visible light. The canister has a removable lid that fits over the outer wall of the canister to form a substantially airtight seal with the inner volume. Thus, when the lid is applied, gas is sealed within the outer wall of the canister. The matrix precursor is mixed and *V. fisheri* are poured into the space between the walls of the canister and cross-linked to form a gel in which the *V. fisheri* are tethered. Additional, non-tethered *V. fisheri* are washed away with water. Thus, a bioluminescent package is made.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number the bare recitation of "two recitations," without other modifiers, means at least two recitations, or two or more recitations). Furthermore, in those instances where a convention analogous to "at least one of A, B and C, etc." is used, in general such a construction is intended in the sense one having skill in the art would understand the convention "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A bioluminescent packaging comprising:
    a package;
    a matrix within the package;
    a population of one or more bioluminescent organisms within the matrix, wherein the population of one or more bioluminescent organisms is determined by a state of a material therein configured to cause the bioluminescent organisms to emit light, wherein the material comprises a source of nutrients for the population of one or more bioluminescent organisms, wherein the population of bioluminescent organisms comprises a quantity of bioluminescent organisms sufficient to emit an observable light signal, and wherein the population of one or more bioluminescent organisms comprises Vibrionaceae; and
    a membrane within the package at least partially covering at least one surface of the matrix, wherein the membrane is permeable to at least one of a liquid or a gas, and wherein at least an area of the membrane is at least 50% transparent to visible light and can allow the observable light produced from the bioluminescent organisms responsive to the state of the material to pass therethrough.

2. The bioluminescent packaging of claim 1, wherein the packaging comprises at least one of a film, a wrap, a spray-coat, a bag, a pouch, a box, a tray, a canister, a container, a bottle, or a jar.

3. The bioluminescent packaging of claim 1, wherein the matrix comprises at least one of a starch, a carbohydrate, a polynucleotide, a protein, a synthetic polymer, or a hydrogel.

4. The bioluminescent packaging of claim 1, wherein the matrix further comprises at least one of a peptide, a casein peptone, a vitamin, a trace element, or a mineral.

5. The bioluminescent packaging of claim 1, wherein the membrane fully covers the at least one surface of the matrix.

6. The bioluminescent packaging of claim 1, wherein the membrane coats the matrix.

7. The bioluminescent packaging of claim 1, further comprising a light filter configured to modify a color of light emitted from the population of bioluminescent organisms.

8. The bioluminescent packaging of claim 1, wherein the bioluminescent packaging is biodegradable.

9. The bioluminescent packaging of claim 1, wherein the population of bioluminescent organisms is at a density that exceeds a minimum quorum-sensing density for the organisms.

10. The bioluminescent packaging of claim 1, wherein the population of bioluminescent organisms is at a density of at least about $10^9$ organisms per milliliter.

11. The bioluminescent packaging of claim 10, wherein the at least one organism produces a reporter molecule the presence of which can serve as an element to be detected.

12. The bioluminescent packaging of claim 10, wherein the at least one organism produces a reporter molecule the absence of which can serve as an element to be detected.

13. The bioluminescent packaging of claim 12, wherein the reporter molecule comprises luciferase.

14. The bioluminescent packaging of claim 1, wherein cross-linking results in restraining the one or more bioluminescent organism to the matrix.

15. The bioluminescent packaging of claim 1, wherein the matrix is at least 85% transparent to light emitted from the population of bioluminescent organisms.

16. The bioluminescent packaging of claim 1, further comprising a food source for the population of bioluminescent organisms.

* * * * *

UNITED STATES PATENT AND TRADEMARK OFFICE
CERTIFICATE OF CORRECTION

PATENT NO. : 9,476,835 B2
APPLICATION NO. : 13/519877
DATED : October 25, 2016
INVENTOR(S) : Manion It is certified that error appears in the above-identified patent and that said Letters Patent is hereby corrected as shown below:

In the Specification

Column 1, Line 6, delete "§371" and insert -- § 371 --, therefor.

Column 1, Line 17, delete "area" and insert -- are a --, therefor.

Column 1, Line 49, delete "tended" and insert -- intended --, therefor.

Column 2, Line 4, delete "not meant," and insert -- not meant --, therefor.

Column 3, Line 2, delete "by or a" and insert -- by a film or a --, therefor.

Column 3, Line 44, delete "4, 5, 8, 9, 10, 1," and insert -- 4, 5, 6, 7, 8, 9, 10, 11, --, therefor.

Column 6, Line 50, delete "and" and insert -- (and --, therefor.

Column 7, Line 46, delete "humidity the ratio" and insert -- humidity (i.e. the ratio --, therefor.

Column 7, Line 58, delete "or 12" and insert -- or 12, --, therefor.

Column 8, Line 31, delete "application, in some" and insert -- application. In some --, therefor.

Column 9, Line 57, delete "organism, in" and insert -- organism. In --, therefor.

Column 11, Line 29, delete "dioxide, decay" and insert -- dioxide, pH, decay --, therefor.

Column 11, Lines 33-34, delete "of material" and insert -- of a material --, therefor.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,476,835 B2

Column 12, Line 42, delete "Inn" and insert -- In --, therefor.

Column 13, Line 54, delete "carbohydrates, it is" and insert -- carbohydrates. It is --, therefor.

Column 16, Line 49, delete "number the bare" and insert -- number (e.g., the bare --, therefor.

Column 16, Line 52, delete "A, B and C," and insert -- A, B, and C, --, therefor.

Column 16, Line 55, delete ""a system" and insert -- (e.g., "a system --, therefor.